US012145905B2

(12) United States Patent
Urbanus et al.

(10) Patent No.: US 12,145,905 B2
(45) Date of Patent: *Nov. 19, 2024

(54) OXIDATIVE PREPARATION OF MALEIC ACID

(71) Applicant: Nederlandse Organisatie voor toegepast-natuurwetenschappelijk onderzoek TNO, 's-Gravenhage (NL)

(72) Inventors: Johan Urbanus, 's-Gravenhage (NL); Marc Crockatt, 's-Hertogenbosch (NL); Earl Lawrence Vincent Goetheer, Mol (BE); Roman Latsuzbaia, Delft (NL)

(73) Assignee: Nederlandse Organisatie voor toegepast-natuurwetenschappelijk onderzoek TNO, 's-Gravenhage (NL)

(*) Notice: Subject to any disclaimer, the term of this patent is extended or adjusted under 35 U.S.C. 154(b) by 643 days.

This patent is subject to a terminal disclaimer.

(21) Appl. No.: 17/414,995

(22) PCT Filed: Dec. 20, 2019

(86) PCT No.: PCT/NL2019/050869
§ 371 (c)(1),
(2) Date: Jun. 17, 2021

(87) PCT Pub. No.: WO2020/130834
PCT Pub. Date: Jun. 25, 2020

(65) Prior Publication Data
US 2022/0064097 A1 Mar. 3, 2022

Related U.S. Application Data

(63) Continuation of application No. PCT/NL2018/050881, filed on Dec. 21, 2018.

(51) Int. Cl.
C07C 51/235 (2006.01)
C25B 3/07 (2021.01)
C25B 3/23 (2021.01)
C25B 11/04 (2021.01)
C25B 11/042 (2021.01)
C25B 11/052 (2021.01)

(52) U.S. Cl.
CPC ............ *C07C 51/235* (2013.01); *C25B 3/07* (2021.01); *C25B 3/23* (2021.01); *C25B 11/04* (2013.01); *C25B 11/042* (2021.01); *C25B 11/052* (2021.01)

(58) Field of Classification Search
None
See application file for complete search history.

(56) References Cited

U.S. PATENT DOCUMENTS 1,709,297 A 4/1929 Yabuta
4,155,920 A 5/1979 Milberger et al.
11,912,656 B2 * 2/2024 Crockatt ............... C07C 51/235
2015/0316557 A1 11/2015 Keillor et al.
2019/0106796 A1 * 4/2019 Choi ..................... C25B 11/04

FOREIGN PATENT DOCUMENTS

| CN | 102372685 A | 3/2012 |
| CN | 102977244 A | 3/2013 |
| CN | 103910699 A | 7/2014 |
| CN | 104119219 B | 10/2014 |
| GB | 253877 A | 1/1927 |
| GB | 297667 | 5/1929 |
| JP | 2002179665 A | 6/2002 |
| JP | 2013126967 A | 6/2013 |
| JP | 2022514771 A | 2/2022 |
| RU | 2455298 | 7/2012 |
| SU | 412176 A1 * | 1/1974 |
| WO | 03048097 A1 | 6/2003 |
| WO | 2010007139 A1 | 1/2010 |
| WO | 2015060827 A1 | 4/2015 |
| WO | 2020130802 A1 | 6/2020 |

OTHER PUBLICATIONS

Milman ("Effect of homogeneous catalysts on the electrochemical synthesis of beta-formylacrylic acid" Elektrokhimiya, vol. 14, issue 10, p. 1555-8, 1978) (Year: 1978).*

"Sulfuric Acid Solution, 1N" (downloaded from https://www.fishersci.ca/shop/products/sulfuric-acid-solution-1n-certified-fisher-chemical-3/p-20572 on Dec. 15, 2023) (Year: 2023).*

Pubchem1 ("2(5H)-Furanone, 5-hydroxy-", National Center for Biotechnology Information (2023). PubChem Compound Summary for CID 21076, 2(5H)-Furanone, 5-hydroxy-. Retrieved Dec. 15, 2023 from https://pubchem.ncbi.nlm.nih.gov/compound/2_5H_-Furanone_-5-hydroxy) (Year: 2023).*

Pubchem2 ("Furfural" National Center for Biotechnology Information (2023). PubChem Compound Summary for CID 7362, Furfural. Retrieved Dec. 15, 2023 from https://pubchem.ncbi.nlm.nih.gov/compound/Furfural) (Year: 2023).*

Pubchem3 ("4-Oxo-2-butenoic acid", National Center for Biotechnology Information (2023). PubChem Compound Summary for CID 74088, 4-Oxo-2-butenoic acid. Retrieved Dec. 15, 2023 from https://pubchem.ncbi.nlm.nih.gov/compound/4-Oxo-2-butenoic-acid) (Year: 2023).*

(Continued)

*Primary Examiner* — Amy C Bonaparte

(74) *Attorney, Agent, or Firm* — Hoffmann & Baron, LLP

(57) ABSTRACT

The invention is directed to a process for the preparation of maleic acid or a derivative thereof. Said process comprising an electrochemical oxidation of a furoic acid compound into maleic acid in an electrolyte solution; and optionally further comprising a step of reacting the maleic acid to the derivative thereof. In an alternative embodiment, said process comprising a first step comprising an electrochemical oxidation in an electrolyte solution of a furanic compound into one or more intermediates; followed by a second step comprising a chemo-catalytic oxidation of said intermediates to provide maleic acid or a derivative thereof.

16 Claims, No Drawings

(56) References Cited

OTHER PUBLICATIONS

Jakovlev machine generated translation (RU 2455298C1, published on Jul. 10, 2012, of record in the IDS filed on Sep. 5, 2023) (Year: 2023).*
Cha ("Combined biomass valorization and hydrogen production in a photoelectrochemical cell" Nature Chemistry, 2015, p. 328) (Year: 2015).*
Loughlin, Wendy A., et al. "Total Synthesis of (±)-Hyphodermins A and D," The Journal of Organic Chemistry, vol. 73, No. 9, pp. 3435-3440 (2008).
Chen, Yingche, et al. "Ring Substituent Effects on the Thiol Addition and Hydrolysis Reactions of N-Arylmaleimides," The Journal of Organic Chemistry, vol. 80, No. 24, pp. 12182-12192 (2015).
Maier, Günther, et al., "Kleine Ringe, 87. Suche Nach Alternativen Wegen ~Zum Tetra-Tert-Butyltetrahedran; Synthese Sterisch Überladener Verbindungen," Liebigs Annalen, vol. 1995, No. 1, pp. 153-160 (1995). (Abstract attached).
Badovskaya, L. A., et al., "Rearrangements and Tautomeric Transformations of Heterocyclic Compounds in Homogeneous Reaction Systems Furfural-H 2 O 2-Solvent," Russian Journal of General Chemistry, vol. 88, No. 8, pp. 1568-1579 (2018).
Barbosa, Luiz Ca, et al. "Phytogrowth Activity of 3-(3-Chlorobenzyl)-5-Arylidenefuran-2 (5H)-Ones," Zeitschrift für Naturforschung, B 64.2, pp. 245-251 (2009).
Salles Jr, Airton G., et al. "A Self-Organizing Chemical Assembly Line," Journal of the American Chemical Society, vol. 135 No. 51, pp. 19143-19146 (2013).
Alonso-Fagundez, Noelia, et al. "Aqueous-Phase Catalytic Oxidation of Furfural with H 2 O 2: High Yield of Maleic Acid by Using Titanium Silicalite-1," RSC Advances, 4.98, pp. 54960-54972 (2014).
Hellstrom, A. N. "Om Elektrolytisk Oxidation av Furfurol," Svensk Kemisk Tidskrift, 60, pp. 214-220 (1948).
Wojcieszak, Robert, et al. "Recent Developments in Maleic Acid Synthesis from Bio-Based Chemicals," Sustainable Chemical Processes, vol. 3.9, pp. 1-11 (2015). DOI 10.1186/s40508-015-0034-5.
Nasman, J-Ah, et al., "An Improved One-Pot Preparation of 2-Furanones," Synthesis (Stuttgart) 8, pp. 786-788 (1985).
Tachibana, Yuya, et al., "Synthesis and Verification of Biobased Terephthalic Acid from Furfural," Scientific Reports vol. 5.1, pp. 1-5 (2015).
Badovskaya, L. A., et al., "Effect of Acid-Base Properties of the Medium on the Reactions in the 2-Furaldehyde-H 2 O 2-H 2 O System with and without VOSO 4," Russian Journal of General Chemistry, vol. 84.6, pp. 1133-1140 (2014).
Milas, Nicholas A., "Fumaric Acid," Organic Syntheses, vol. 11, pp. 46-48 (2003).
Nasman, Jan H., "3-Methyl-2 (5H)-furanone: 2 (5H)-Furanone, 3-Methyl-." Organic Syntheses 68 (2003): 162-174. DOI:10.15227/orgsyn.068.0162.
Cao, Ruzhen, et al. "A Convenient Synthesis of 2 (5H)-Furanone," Organic Preparations and Procedures International, vol. 28.2, pp. 215-216 (1996).
Kemppainen, Eeva K., et al. "Mukaiyama-Michael Reactions with Acrolein and Methacrolein: A Catalytic Enantioselective Synthesis of the C17-C28 Fragment of Pectenotoxins," Organic Letters, vol. 14, No. 4, pp. 1086-1089 (2012).
Song, Liyan, et al. "Asymmetric Total Syntheses of (-)-Penicipyrone and (-)-Tenuipyrone via Biomimetic Cascade Intermolecular Michael Addition/Cycloketalization," Organic letters vol. 15, No. 1, pp. 6-9 (2013).
Milman, V. I., et al., "Determination of the Parameters of Electrochemical Furfural Oxidation at a Carbon Electrode in a Continuous Cell," Soviet Electrochemistry, vol. 22.12, pp. 1539-1540 (1986).
Mil'man, V. I., et al., "Effect of Homogeneous Catalysts on the Electrochemical Synthesis of b-formylacrylic Acid," Elektrokhimiya, vol. 14, Issue 10, pp. 1555-1558 (1978). ISSN: 0424-8570.
Badovskaya, L. A. "New Reaction for the Preparation of Lower Oxodihydrofurans," Chemistry of Heterocyclic Compounds, vol. 14, No. 10, pp. 1062-1067 (1978).
Milas, Nicholas A. "Catalytic Oxidations in Aqueous Solutions I. The Oxidation of Furfural," Journal of the American Chemical Society, vol. 49.8, pp. 2005-2011 (1927).
Guo, Huajun, et al., "Catalytic Aerobic Oxidation of Renewable Furfural with Phosphomolybdic Acid Catalyst: An Alternative Route to Maleic Acid," The Journal of Physical Chemistry C, vol. 115.35 pp. 17516-17522 (2011).
Menegazzo, Federica, et al. "Structure-Activity Relationships of Au/ZrO2 Catalysts for 5-Hydroxymethylfurfural Oxidative Esterification: Effects of Zirconia Sulphation on Gold Dispersion, Position and Shape," Journal of Catalysis, vol. 326, pp. 1-8 (2015).
Menegazzo, Federica, et al. "On the Process for Furfural and HMF Oxidative Esterification over Au/ZrO2," Journal of Catalysis, vol. 319, pp. 61-70 (2014).
Casanova, O., S., et al. "Biomass into Chemicals: One Pot-Base Free Oxidative Esterification of 5-Hydroxymethyl-2-Furfural into 2,5-Dimethylfuroate with Gold on Nanoparticulated Ceria," Journal of Catalysis, vol. 265, No. 1, pp. 109-116 (2009).
Gassama, Abdoulaye, et al., "Synthesis of Surfactants from Furfural Derived 2 [5H]-Furanone and Fatty Amines," Green Chemistry, vol. 12, No. 5, pp. 859-865 (2010).
Lan, Jihong, et al. "Catalytic Aerobic Oxidation of Renewable Furfural to Maleic Anhydride and Furanone Derivatives with Their Mechanistic Studies," Green Chemistry, vol. 16, No. 9, pp. 4351-4358(2014).
Tachibana, Yuya, et al., "Synthesis and Characterization of a Renewable Polyester Containing Oxabicyclic Dicarboxylate Derived from Furfural," Green Chemistry, vol. 15 No. 5, pp. 1318-1325 (2013).
Zhao, Wen-Tao, et al. "Use of Submerged Anaerobic-Anoxic-Oxic Membrane Bioreactor to Treat Highly Toxic Coke Wastewater with Complete Sludge Retention," Journal of Membrane Science, vol. 330, No. 1-2, pp. 57-64 (2009). (Abstract).
Poskonin, V. V. "Catalytic Oxidation Reactions of Furan and Hydrofuran Compounds 9.* Characteristics and Synthetic Possibilities of the Reaction of Furan with Aqueous Hydrogen Peroxide in the Presence of Compounds of Niobium (ii) and (v)," Chemistry of Heterocyclic Compounds, vol. 45, No. 10, pp. 1177-1183 (2009).
Badovskaya, L. A., et al. "Catalytic Oxidation of Furan and Hydrofuran Compounds. 7. Production of 2 (5H)-Furanone by Oxidation of Furfural with Hydrogen Peroxide and Some of its Transformations in Aqueous Solutions," Chemistry of Heterocyclic Compounds, vol. 38, No. 9, pp. 1040-1048 (2002). (Abstract).
Choudhary, H., et al., "Highly Efficient Aqueous Oxidation of Furfural to Succinic Acid Using Reusable Heterogeneous Acid Catalyst with Hydrogen Peroxide," Chem. Lett., The Chemical Society of Japan, pp. 409-411 (2011).
Choudhary, H., et al., "Highly Efficient Aqueous Oxidation of Furfural to Succinic Acid Using Reusable Heterogeneous Acid Catalyst with Hydrogen Peroxide," Chem. Lett., The Chemical Society of Japan (2011). (Supporting Information).
Alonso-Fagundez, Noelia, et al. "Selective Conversion of Furfural to Maleic Anhydride and Furan with VOx/Al2O3 Catalysts," ChemSusChem, vol. 5, No. 10, pp. 1984-1990 (2012).
Deng, Jin, et al. "Aerobic Oxidation of Hydroxymethylfurfural and Furfural by Using Heterogeneous CoxOy—N@ C Catalysts," ChemSusChem, vol. 7, No. 12. pp. 3334-3340 (2014), supporting information only.
Shi, Song, et al., "Synthesis of Maleic Acid from Renewable Resources: Catalytic Oxidation of Furfural in Liquid Media with Dioxygen," Catalysis Communications, vol. 12, No. 8, pp. 731-733 (2011).
Hjelmgaard, Thomas, et al. "Synthesis of Furanone-Based Natural Product Analogues with Quorum Sensing Antagonist Activity," Bioorganic & Medicinal Chemistry, vol. 11, No. 15, pp. 3261-3271 (2003).
Tachibana, Yuya, et al. "Chemical Synthesis of Fully Biomass-Based Poly (Butylene Succinate) from Inedible-Biomass-Based Furfural and Evaluation of its Biomass Carbon Ratio," Biomacromolecules, vol. 11, No. 10, pp. 2760-2765 (2010).
Fan, Guo-Zhi, "Study on the New Technology of Synthesis of Dimethyl Fumarate," Applied Chemical Industry, vol. 33, No. 3 (Jun. 2004).

(56) References Cited

OTHER PUBLICATIONS

Choudhary, Hemant, et al., "Metal-Free Oxidative Synthesis of Succinic Acid From Biomass-Derived Furan Compounds Using a Solid Acid Catalyst with Hydrogen Peroxide," Applied Catalysis A: General, vol. 458, pp. 55-62 (2013).

Li, Fengbo, et al. "Pt Nanoparticles Over $TiO_2$—$ZrO_2$ Mixed Oxide as Multifunctional Catalysts for an Integrated Conversion of Furfural to 1, 4-Butanediol," Applied Catalysis A: General, vol. 478, pp. 252-258 (2014).

Robert, Carine, et al., "Facile and Efficient Synthesis of Cyclic Anhydrides from Dicarboxylic Acids," ACS Catalysis, vol. 4, No. 10, pp. 3586-3589 (2014).

Lan, Jihong, et al. "Transformation of 5-Hydroxymethylfurfural (HMF) to Maleic Anhydride by Aerobic Oxidation with Heteropolyacid Catalysts," ACS Catalysis, vol. 5, No. 4, pp. 2035-2041 (2015). DOI: 10.1021/cs501776n.

Tachibana, Yuya, et al. "Synthesis of Biomass-Based Monomers from Biomass-Based Furfural for Polyesters and Evaluation of Their Biomass Carbon Ratios," Biobased Monomers, Polymers, and Materials, American Chemical Society (2012). 91-110. DOI: 10.1021/bk-2012-1105.ch007.

Kubota, Stephen R., et al., "Electrochemical Valorization of Furfural to Maleic Acid," ACS Sustainable Chemistry & Engineering, vol. 6, No. 8, pp. 9596-9600 (2018).

\* cited by examiner

OXIDATIVE PREPARATION OF MALEIC ACID

CROSS-REFERENCE TO RELATED APPLICATIONS

This application is a U.S. National Phase application of International Application No. PCT/NL2019/050869, filed Dec. 20, 2019, which claims priority to International Application No. PCT/NL2018/050881, filed Dec. 21, 2018, the disclosures of which are incorporated herein by reference.

The invention is in the field of the chemical preparation of maleic acid and derivatives thereof. In particular, the invention is directed to a sustainable chemical preparation of maleic acid and derivatives thereof using starting materials derivable from biomass.

Current industrial processes for the production of maleic acid are typically based on the oxidation of petrochemicals such as butane or benzene. It is desired to replace petrochemicals with chemicals that are based on biomass in order to reduce the environmental footprint of the production and to provide a more sustainable route to maleic acid, see e.g. Wojcieszak et al., *Sustainable Chemical Processes*, 2015, 3:9, 1-11 For instance, in *Journal of Organic Chemistry*, 1986, 51(4), 567-569; the chemical oxidation of furfural, a biomass-derivable chemical, with hydrogen peroxide is disclosed. A drawback of such chemical oxidation reactions is the requirement of hydrogen peroxide as the oxidation agent, as this must be prepared in a separate production process. As such, the overall advantage of using a biomass-derivable chemical is reduced. Alternatively, the furfural may be oxidized electrochemically, as is disclosed in GB253877, Mil'man et al., *Elektrokhimiya*, 1978, Volume: 14, Issue: 10, 1555-1558 and Hellström: *Svensk Kemish Tidskrift*, 1948, Volume 60, 214-220. However, a drawback of both these known methods for preparing maleic acid is that furfural is used as the starting material, and the one-pot oxidation process is time consuming and typically requires the presence of a mediator to achieve acceptable reaction rates. Mediators however, add expense and are often difficult to recycle, and therefore generally not preferred in large scale procedures.

In addition, furfural is relatively unstable, which means that it typically contains significant levels of impurities, because of which the color changes rapidly after distillation (for instance to orange/brown). The instability is particular problematic in a continuous system wherein impurities concentration increases due to recycling. As such, more purification (and, as such, costs) will be required in recycling loops with dirty inputs. Furthermore, these impurities can also cause problems with the desired reaction. They can also vary from batch to batch which results in unpredictable results.

Accordingly, it is preferred to provide a process for the preparation of maleic acid that does not suffer, or at least suffers less from one or more of these drawbacks. The present inventors found that this can be achieved by essentially two different types of processes, each using a furanic compound comprising an 2-carbonyl substituent (hereinafter also referred to as the furanic compound). The furanic compound can by illustrated by formula I, wherein $R^1$ is H, $CH_2OH$, $CO_2H$ or CHO and $R^2$ is H, OH, $C_1$-$C_6$ alkyl or $O(C_1$-$C_6$ alkyl). Esters, amides, acid halides, anhydrides, carboximidates, nitriles, and salts of the compound according to formula I are herein meant to be comprised by the term furanic compound.

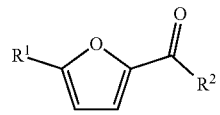

I

In a first aspect of the present invention, the process for the preparation of maleic acid or a derivative thereof comprises a one-step electrochemical oxidation of a furanic compound into maleic acid, which electrochemical oxidation is carried out in an electrolyte solution comprising a mediator. This process is illustrated in Scheme 1, wherein said furanic compound is a compound according to formula I wherein $R^1$ is H, $CO_2H$, $CH_2OH$ or CHO and $R^2$ is H, OH, $C_1$-$C_6$ alkyl or $O(C_1$-$C_6$ alkyl), or esters, amides, acid halides, anhydrides, carboximidates, nitriles, and salts thereof.

Scheme 1

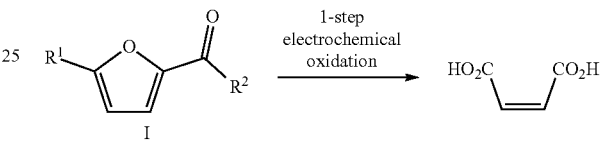

The process optionally further comprising a step of reacting the maleic acid to the derivative thereof.

The present inventors found that this process particularly benefits from the presence of the mediator, especially for large scale applications. Suitable mediators are described herein-below. Without the mediator being present, the reaction rate is too low to be suitably applied on large scale. Without wishing to be bound by theory, the present inventors believe that the reason for this low rate can be found in the formation of one or more intermediates, of which the electrochemical oxidation proceeds particularly slow. It is believed that these intermediates comprise cis-β-formylacrylic acid (also referred herein as formyl-acrylic acid), which can under certain condition be in a tautomeric equilibrium with 5-hydroxy-2(5H)-furanone.

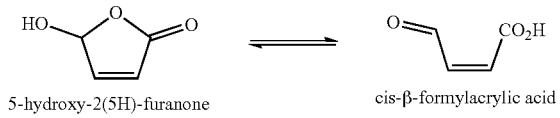

5-hydroxy-2(5H)-furanone      cis-β-formylacrylic acid

It is postulated that the closed ring from (i.e. the 5-hydroxy-2(5H)-furanone) cannot, or only very slowly, be electrochemically oxidized and that as such, this oxidation is hampered. At the preferred pH of the reaction, the equilibrium lies almost completely at the side of the furanone, so slow reaction occurs. In order to achieve an acceptable reaction rate, the mediator is preferably present.

However, the presence of a mediator however is particularly on a large scale not preferred. Typical mediators are costly and large-scale processes would require recycling or immobilization of the mediator for the process to be economically feasible. For this reason, immobilization of the mediator is preferred, in particular for the process comprising the one-step electrochemical oxidation. Most preferably, the mediator is immobilized in the close vicinity or at the working electrode (vide infra for additional details on the electrodes). Nevertheless, drawbacks of immobilization remain probably leaching of the mediator and the fact that immobilization limits the amount of mediator available (since the surface area of any support would be limited), which would also limit the rate on large scale.

Examples of suitable immobilized mediators at the electrode include doping the working electrode with a mediator (vide infra). The inventors surprisingly found that a vanadium-doped electrode is particularly suitable for carrying out this process. Accordingly, the vanadium-doped electrode is another aspect of the present invention. In this embodiment, it is preferred that the pH of the electrolyte solution is in the range of 3 to 7, more 5 to 6 to limit leaching of the vanadium. A drawback of this approach is however, that the process to prepare maleic acid is preferably carried out at a lower pH (i.e. typically below 5), such that the free acid ($CO_2H$) is obtained instead of a salt thereof. In addition, the use and immobilization of the mediator remains costly, cumbersome and thus unfavorable.

In view of the remaining drawbacks and challenges of the one-step electrochemical oxidation according to the invention, another aspect of the invention, which includes a two-step approach is preferred. This particular aspect of the invention is directed to a process that comprises a first step comprising an electrochemical oxidation in an electrolyte solution of the furanic compound into one or more intermediates, followed by a second step comprising a chemo-catalytic oxidation of said intermediates into maleic acid or derivatives thereof such as maleic anhydride. In the context of the present invention, the chemo-catalytic oxidation can be considered a non-electrochemical oxidation. Other examples of non-electrochemical oxidation that can suitably be used for this invention included photochemical oxidation and photoelectrochemical oxidation.

The process using the two-step approach (herein also referred to as the two-step process) is illustrated in Scheme 2.

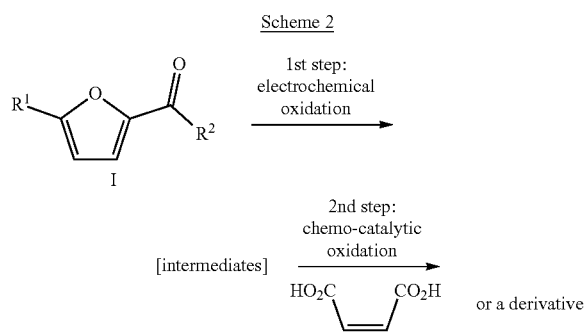

Scheme 2

Again, the process optionally further comprising a step of reacting the maleic acid to the derivative thereof. As described herein-above, said one or more intermediates typically comprise 5-hydroxy-2(5H)-furanone and/or cis-β-formylacrylic acid.

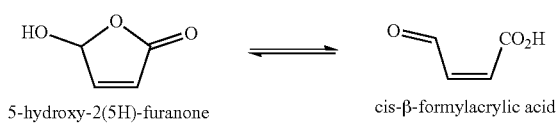 [SMILES: O=C1C=CC(O)O1 ; O=C/C=C\C(=O)O]

5-hydroxy-2(5H)-furanone    cis-β-formylacrylic acid

An advantage of the two-step process is that no mediator is required. Accordingly, the electrolyte solution is preferably essentially free of a mediator.

The inventors surprisingly found that, in contrast to electrochemical oxidation, chemo-catalytic oxidation of formyl-acrylic acid proceeds relatively easily. Typical, conventional conditions for oxidation of aldehydes into carboxylic acids can be used. Suitable oxidizing agents in this respect may be chlorates, permanganates, hydrogen peroxide and the like. These methods however may be accompanied by undesired salt generation in the process. The present inventors have however surprisingly found that 5-hydroxy-2(5H)-furanone and/or cis-β-formylacrylic acid can be oxidized to maleic acid or a derivative thereof by molecular oxygen ($O_2$), also referred to as oxygen. Accordingly, the chemo-catalytic oxidation can be carried out by using oxygen as an oxidation agent in the presence of a catalyst. Suitable oxidation catalysts in this respect comprise transition metals such as palladium, copper and/or platinum supported on activated carbon, as is further detailed below.

Accordingly, in a particular embodiment of the present invention, the process comprising a step of oxidizing 5-hydroxy-2(5H)-furanone and/or cis-β-formylacrylic acid to maleic acid or a derivative thereof by contacting 5-hydroxy-2(5H)-furanone and/or cis-β-formylacrylic acid with molecular oxygen ($O_2$) in the presence of a catalyst, said step herein referred to as the second step with $O_2$.

The inventors have found that several metals, in particular transition metals can suitably catalyze the oxidation reaction in the second step with $O_2$. Particular good results were obtained with copper, gold, palladium, platinum and ruthenium, especially gold.

The catalyst preferably further comprises a solid support. The solid support may be a support known in the art and generally any support may be suitable, provided that it is not detrimental to the oxidation reaction. Typically, the solid support is inert in the second step with $O_2$. Examples of support that we found to be suitable for the present invention include activated carbon, aluminum oxide, zinc oxide, and titanium dioxide. Titanium dioxide as a solid support, in particular in combination with gold gave particular good results in term of maleic acid yield.

The second step with $O_2$ of the present invention is generally carried out in a liquid and not in a gaseous phase. Due to the instability of furanic compounds and of HFO at the high temperatures which are required to maintain the compounds in gaseous form, gaseous phase reaction conditions are not well suitable for the present invention. It is accordingly preferred that the HFO and/or formyl-acrylic acid is/are liquid or dissolved in a solvent when contacted with $O_2$. Suitable solvents include both organic and aqueous solvents. For reasons elaborated herein-below, water-immiscible organic solvents and acidic aqueous solvents are particularly preferred. Good conversion of HFO and/or formyl-acrylic acid was obtained in water, aqueous sulfuric acid, acetic acid, ethyl acetate, methyl isobutyl ketone (MIBK), methyl tert-butyl ether (MTBE), 2-methyl tetrahydrofuran (2-MeTHF), dichloromethane, heptane, acetonitrile, acetone, nitromethane and toluene, preferably 2-MeTHF, toluene and MTBE.

The solvent in which the second step with $O_2$ may be carried out, can have an influence on the product that is formed. For instance, in organic solvents, maleic anhydride may be formed by an in situ dehydration reaction of maleic acid or when HFO is directly oxidized by the catalyst. At the other hand, in an aqueous solvent, maleic acid itself is typically formed under acidic conditions, while a salt of maleic acid can be formed under basic conditions. Under certain reaction conditions, maleic acid may also, at least partially, isomerize to fumaric acid. The reaction conditions under which the second step with $O_2$ is carried out, typically also influence the product that is formed.

The oxidation process was found to give the best results in terms of conversion under moderate reaction conditions, including slightly elevated temperature and pressure. Accordingly, the second step with $O_2$ is preferably carried out under a pressure of at least 5 bar, preferably at least 10 bar. Preferred temperature ranges to carry out the second step with $O_2$ are 20 to 200° C., more preferably in 50 to 150° C., most preferably 60 to 100° C. These conditions allow the reaction to be carried out in a continuous reaction, such as a tube reactor, which is preferred. The reactor may accordingly comprise a fixed catalyst bed comprising the catalyst.

The starting materials HFO and/or formyl-acrylic acid can be supplied or provided in the second step with $O_2$ in an isolated (i.e. essentially pure) formulation or in a reaction mixture that originating from a preceding process. The isolated formulation can be obtained by a preceding process and isolation that is not part of the present invention. This preceding reaction can be any type of reaction process and could for instance have served to produce HFO and/or formyl-acrylic acid as main products, or HFO and/or formyl-acrylic acid could have been produced therein as side products. In a preferred embodiment of the present invention, HFO and/or formyl-acrylic acid originate from one or more furanic compounds having a biomass origin.

It was found that carrying out the second step with $O_2$ in accordance with the present invention in combination with the electrochemical oxidation of the furanic compound is especially beneficial, as it was found that a preferred pH of the electrochemical oxidation, the equilibrium between HFO and formyl-acrylic acid lies almost completely at the side of the HFO, so slow oxidation occurs. Although an acceptable reaction rate in the electrochemical oxidation can be achieved by applying a mediator, the presence of a mediator however is particularly on a large scale not preferred. Typical mediators are costly and large-scale processes would require recycling or immobilization of the mediator for the process to be economically feasible. The second step with $O_2$ according to the present invention shows good reaction of HFO and formyl-acrylic acid and as such, a two-step process including the first step in combination with the second step with $O_2$ is overall preferred.

It may be appreciated that during the first step of the two-step process, some amount of maleic acid can be formed before all the starting material is consumed because the conditions of the first step can still enable this conversion, albeit in a relatively low rate.

The chemo-catalytic oxidation is preferably carried out a slightly elevated temperature. A temperature in the range of 20 to 150° C., preferably in the range of 30 to 130° C., more preferably in the range of 50 to 100° C. is typically suitable. Under these conditions, a reaction time of a few hours (e.g. 1 to 4 hours) is generally enough to reach full conversion.

In case the first step is carried out in an aqueous electrolyte solution (which is preferable, vide infra), the second step can be carried out in the same solution, in the same solution but after a shift in pH, or after extraction of said intermediates with an organic solvent. For the latter embodiment, it is preferably to carry out said second step in said organic solvent. It may be appreciated that this embodiment covers processes in which the organic extraction is subjected to intermediate drying, and those in which it is not dried before further use. Typical organic solvents are suitable, as long as these do not react in the chemo-catalytic oxidation or are otherwise detrimental to this step. Examples of organic solvents that can be used include dichloromethane, toluene, ethyl acetate, 2-methyltetrahydrofuran and the like. In this particular embodiment, maleic anhydride may be obtained directly from the process without a separate subsequent dehydration step. It may also be possible to carry out the chemo-catalytic oxidation in an alcohol to get the mono and/or di-ester of maleic acid directly.

In an embodiment of the present invention wherein the first en second step are carried out in the same solution, the process further comprises a step of isolating the maleic acid or the derivative thereof to provide the isolated maleic acid or derivative thereof, and a used electrolyte solution. The used electrolyte solution can then be recycled into the process. The used electrolyte solution may contain residual furanic compound, intermediates of the process, maleic acid, and any other impurities and/or polymers that are formed. Accordingly, it may be preferred to purify the used electrolyte solution prior to recycling (e.g. nano-filtration to remove polymeric materials). Alternatively or additionally to the purification, it may be preferred to bleed some of the recycled electrolyte and add fresh material to maintain a constant quality of the electrolyte.

Isolation of the maleic acid or the derivative thereof can be carried out using standard isolation techniques such as distillation and the like. The specifically preferred method of isolation may depend on the used solvent. By isolation of the maleic acid, the pH of the electrolyte solution can also be restored to the original pH, i.e. the pH at the start of the oxidation. As such, no pH adjustment by additives may be required. In case some electrolyte, acid, solvent or water is lost or consumed during the oxidation of the furanic compound or the isolation of the maleic acid, the acid, solvent or water can be replenished during the recycling of the electrolyte solution.

Recycling of the electrolyte solution is particularly preferred when the present process is a continuous process and for instance carried out in a continuous reactor system. The reactor system in which the process is carried out can accordingly comprise a recycle loop for the electrolyte solution. Recycling the electrolyte solution may advantageously result in a minimal chemical waste production and a reduced external input.

Performing the second step in alkaline solvents at high pH (e.g. more than 7) gives very high yields of the maleic acid salt.

Both aspects of the present invention share many features and properties. It may be appreciated that for sake of conciseness and clarity, although not all features may necessarily be explicitly attributed to the individual aspects, all features described herein can be used for both aspects, unless it logically follows or is explicitly indicated otherwise.

In addition, it may be appreciated that the second step can be carried out separately from the first step. As such, chemo-catalytic oxidation of the intermediates, in particular of 5-hydroxy-2(5H)-furanone and/or cis-β-formylacrylic acid, as such is also part of the present invention.

As is described herein-above, a 2-furoic acid compound (herein also referred to as furoic acid) is advantageously more stable than furfural and can be available as a side-product in the production of 2,5-furandicarboxylic acid (FDCA) or obtained by stabilization of furfural by direct oxidation to furoic acid, which is generally a clean high yielding process at mild conditions (e.g. at reaction temperature of less than 100° C.). As such, the use of a 2-furoic acid compound is preferred. Moreover, the application of furoic acid in chemical processes in accordance with the present invention is also beneficial since it is believed that there are currently no significant markets envisaged for furoic acid.

The present inventors surprisingly found that the use of furoic acid to produce maleic acid and the replacement of furfural by furoic acid, is particularly advantageous in electrochemical oxidation reaction. Electrochemical reactions tend to have significantly longer residence times than thermochemical reactions (due to limitations in the surface area of the electrodes, and mass transfer to/from the surface, vide infra), so the chemical materials are often a lot longer in solution where they are prone to decompose. Therefore, the electrochemical oxidation process to prepare maleic acid benefits particularly from an increase stability of the starting material. Accordingly, the oxidation comprises, or for the first aspect preferably consists of, an electrochemical oxidation in an electrolyte solution, typically an aqueous electrolyte solution comprising said furoic acid compound. As such the addition of an oxidation agent such a hydrogen peroxide may not be required. Typically, said process comprises dissolving a furoic acid compound in the electrolyte solution, followed by the electrochemical oxidation to convert said furoic acid or derivative thereof into maleic acid.

A particular embodiment of the present invention comprises chemo-catalytic oxidation of furfural to furoic acid, prior to carrying out the electrochemical oxidation of furoic acid.

With the furoic acid compound is meant any compound that is based on 2-furoic acid and has the same oxidation state as furoic acid such that it can be oxidized to maleic acid. Examples of suitable furoic acid compounds include 2-furoic acid, furoic acid esters, furoic acid amides, furonitrile, anhydrides of furoic acid, carboximidates of furoic acid, furoic acid halides and salts of furoic acid. In particular because of its good solubility in water (about 37.1 g/L in water at 15° C. and about 100 g/L in water at 50° C.), 2-furoic acid is preferably used as the furoic acid compound.

It was found that maleic acid can directly be obtained from the oxidation process in accordance with the present invention, in particular when the process is carried out in an aqueous environment. This is in contrast to the conventional oxidation processes that are based on benzene and butane, wherein maleic anhydride is initially obtained and only in a subsequent hydrolysis step can be converted to maleic acid. However, like maleic acid, maleic anhydride is also a chemical of industrial application and therefore it may be preferred that the present process includes the preparation of maleic acid derivatives such as maleic anhydride. As such, the present process optionally includes a step of further reacting the maleic acid to a derivative thereof, such as maleic anhydride. If the present process is carried out at least partially in an organic solvent and preferably under anhydrous conditions, then maleic anhydride may be obtained directly from the process without a separate subsequent dehydration step.

The direct formation of maleic anhydride from the chemo-catalytic oxidation, as illustrated in Scheme 3, is a particular preferred embodiment of the present invention.

Scheme 3

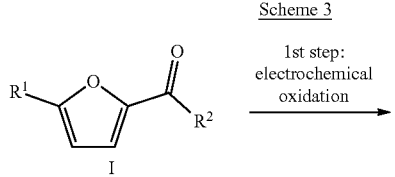

1st step: electrochemical oxidation

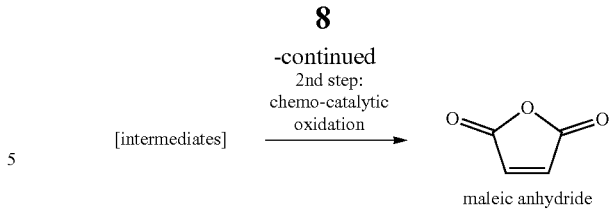

maleic anhydride

Derivatives of maleic acid that can be obtained in the step of further reacting the maleic acid may comprise fumaric acid, succinic acid, and salts, esters, anhydrides, amides or imides thereof. This optional further reaction step to provide maleic anhydride, fumaric acid, succinic acid or salts, esters or anhydrides thereof as such (i.e. without the preceding oxidation of furanic compound) is known in the art. For instance, maleic anhydride, fumaric acid and succinic acid can be obtained from maleic acid via a dehydration reaction, an isomerization reaction and a partial hydrogenation reaction, respectively. Fumaric acid is currently produced (predominantly) on an industrial scale by the catalytic isomerization of maleic acid. Succinic acid is also produced industrially from partial reduction of maleic acid, although this is one of several known routes.

As described above, the inventors furthermore surprisingly found that the electrochemical oxidation of the furanic compound to maleic acid can possibly proceed through cis-β-formylacrylic acid (also referred herein as formylacrylic acid) as an intermediate, which can under certain condition be in a tautomeric equilibrium with 5-hydroxy-2(5H)-furanone. Accordingly, another aspect of the present invention is the preparation of cis-β-formylacrylic acid and/or 5-hydroxy-2(5H)-furanone from the furanic compound. The cis-β-formylacrylic acid and/or 5-hydroxy-2(5H)-furanone prepared with the electrochemical oxidation according to the present invention can be isolated or can be further reacted to the maleic acid or a derivative thereof. This further reaction can also be carried out electrochemically, in particular electrochemically in accordance with the process and parameters as described herein. Alternatively, as described herein-above, the cis-β-formylacrylic acid and/or the 5-hydroxy-2(5H)-furanone can be further oxidized to maleic acid and/or maleic anhydride with the chemo-catalytic oxidation such as oxygen-based thermochemical oxidation type conditions, biotechnological processes or photo-oxidation. This may particularly be preferred in case the electrochemical oxidation of the furanic compound to maleic acid is rate limited in the conversion of the cis-β-formylacrylic acid and/or the 5-hydroxy-2(5H)-furanone to maleic acid and for large-scale processes wherein the use of mediator is not preferred.

The electrochemical oxidation according to the present invention is preferably carried out using one or more working electrodes (herein also referred to as the anodic electrode, anode or simply the electrode) comprising lead oxide, for instance $PbO_2$ which lead oxide may optionally supported on a metal such as Pb, a porous graphite such as activated carbon, carbon nanotubes (CNT), reticulated vitreous carbon (RVC) or carbon felt, or boron doped diamond (BDD). Activity of the electrode may be improved by adding dopants or adatoms (to the electrode or electrolyte). For instance, addition of metal ions such as $Fe^{2+}$ or $Fe^{3+}$ into the electrolyte can improve stability of $PbO_2$. In principle any electrode structure may be used, including 2D and 3D structures, but one or more electrodes comprising one or more porous electrodes, fusion electrodes, mesh electrodes, nanostructured electrodes, metal or metal oxide particles supported on porous carbon/graphite electrodes or a combination thereof are preferred. Such an electrode result in higher conversion rates. In a particular embodiment, the working electrode may alternatively or additionally comprise one or more of mixed metal oxide (MMO), dimensionally stable anodes (DSA), stainless steel, brass-carbon based graphitic electrodes, Pt, Au, Ag, Cu, Ir, Ru, Pd, Ni, Co, Zn, Cd, In, Sn, Ti, Fe and alloys or oxides thereof.

The counter electrode (also referred to as cathodic electrode or cathode) may comprise one or more materials selected from the group consisting of Au, Pt, Pd, Ir, Ru, Ni, Co, stainless steel, Cu, Carbon, Pb, Ti or alloys thereof. Advantageously, the present process may also comprise paired electro-synthesis to enable co-currently an electrochemical reduction, e.g. production of hydrogen from water, reduction of oxygen to water, or conversion of furfural to furfuryl alcohol, at the cathode.

In a particular embodiment, the working electrode is doped with a mediator (vide infra). The inventors surprisingly found that a vanadium-doped electrode is particularly suitable for carrying out this process. Accordingly, the vanadium-doped electrode is another aspect of the present invention. In this embodiment, it is preferred that the pH of the electrolyte solution is in the range of 3 to 7, more 4 to 5 to limit leaching of the vanadium.

The oxidation of the furanic compound can be carried out directly at the electrode. This means that the electrons from the oxidation agent or electrode are directly transferred to the furanic compound or a chemical intermediate in the reaction. Alternatively, the oxidation can be carried out by using a mediator that receives and temporarily retains the electrons from the electrodes to subsequently transfer the electrons to the furanic compound (or the chemical intermediate in the reaction). Although, the presence of the mediator may not exclude oxidation at the electrode, the oxidation typically predominantly proceeds through the mediator if this is present. Preferably the mediator comprises one or more of vanadates, vanadium oxides (e.g. $V_2O_5$, $VO_2$), molybdates ($MoO_4^{2-}$), chromates ($CrO_4^{2-}$), dichromates ($Cr_2O_7^{2-}$), permanganates ($MnO_4^-$) manganates ($MnO_4^{2-}$), manganese salts ($Mn^{2+}$), tungstates ($WO_4^{2-}$), iodates ($IO_3^-$), chlorates ($ClO^-$), chloride-chlorine couple ($Cl^-/Cl_2$), bromates ($BrO^-$), bromide-bromine couple $Br^-/Br_2$, peroxydisulfates ($S_2O_8^{2-}$) ozone ($O_3$), cobalt salts ($Co^{2+}/Co^{3+}$), cerium salts ($Ce^{3+}/Ce^{4+}$), and the like. Most preferably, the mediator comprises vanadium oxide, sodium molybdate, and/or potassium dichromate.

Surprisingly, it was found by the present inventors that the oxidation reaction also proceeds satisfyingly without any mediator being present. For reasons of costs, safety issues (mediators are often highly toxic/carcinogenic), increased process complexity (recapturing/recycling of the mediator), and the environmental footprint of the process, it may be preferred that the process is carried out without said mediator. Accordingly, the electrolyte solution is preferably essentially free of said mediator during the electrochemical oxidation. In the context of the present invention, essentially free means preferably less than 5 mol %, preferably less than 1 mol %, more preferably less than 0.01 mol % based on the amount of furanic compound starting material present at the start of the electrochemical oxidation reaction. Most preferable, the electrolyte solution comprises trace amounts or less of the mediator. With "at the start of the electrochemical oxidation reaction" is meant the moment just before the first amount of furanic compound will be oxidized.

The oxidation, in particular the electrochemical oxidation, proceeds particularly well at a certain pH-range. The specifically preferred 20 pH-range can i.a. depend on the used electrode or the oxidation agent, but the $pK_a$-values of the furanic compound may also partially determine the preferred pH-range. In particular when the furanic compound comprises 2-furoic acid, the electrochemical oxidation is preferably at least partially carried out at a pH of less than 7, more preferably less than 4, even more preferably less than 3, most preferably about equal or less than 2.

Due to the conversion of the furanic compound into maleic acid, the pH of the electrolyte solution can drop below its value as it was at the start of the reaction. Therefore, it may be possible to start the electrochemical oxidation at a pH-value above the optimal value at which the oxidation can be carried out and that during the conversion of the furanic compound, the pH-value decrease to the optimal pH-value or to the preferred pH-values as defined above. Therefore, the preferred pH-values are defined for at least part of the duration of the electrochemical oxidation (vide supra: "at least partially carried out at a pH of . . . ") and not necessarily for the entire duration of the electrochemical oxidation.

The pH can be adjusted from an external source during the process to maintain the optimal pH during the whole reaction (e.g. addition of a suitable acid or base). Furthermore, it might also be carried out in the presence of a buffer to maintain pH. In addition, the desired pH-range can be set by using an appropriate solvent or appropriate electrolyte solution. Accordingly, it is preferred that the solvent or electrolyte solution, if present, comprises an acid such as an organic and/or a mineral acid. A mineral acid is preferred since, compared to organic acids, mineral acids are more inert in the electrochemical oxidation reaction and therefore preferred. More preferably, the mineral acid is selected from the group consisting of hydrochloric acid (HCl), nitric acid ($HNO_3$), phosphoric acid ($H_3PO_4$), sulfuric acid ($H_2SO_4$), boric acid ($H_3BO_3$), hydrofluoric acid (HF), hydrobromic acid (HBr), perchloric acid ($HClO_4$), hydroiodic acid (HI). Most preferably the electrolyte solution comprises sulfuric acid. In certain embodiments, the acid can be at least partially immobilized by incorporating it into a resin (such as Amberlyst™ or Nafion™), which could be added to the mixture, and/or the acid can be structurally incorporated into the one or more electrodes. In certain embodiments, it may be preferred that the electrolyte comprise the acid in combination with an inorganic salt to increase the ionic conductivity of the electrolyte. For instance, if the pH of the electrolyte is desired to be 1, the concentration of the acid may not be sufficient to provide good conductivity and the additional of salt to that end may be preferred.

The electrolyte solution can be aqueous or non-aqueous. Suitable non-aqueous electrolyte solutions comprise one or more solvents selected from the group consisting of acetone, sulfolane, dimethylsulfoxide (DMSO), tetrahydrofuran (THF), dimethylformamide (DMF), N-methylpyrrolidone (NMP), hexamethylphosphoricacid-triamide (HMPA), acetonitrile (MeCN), dichloromethane (DCM), propylene carbonate, hexafluoroisopropanol (HFIP), and ionic liquids (for instance $[C_4mim]^+$) with anions $HSO_4^-$, $CF_3CO_2^-$, $H_2PO_4^-$, $Cl^-$, $NO_3^-$, $BF_4^-$, $OTf^-$, $PF_6^-$). In particular for the embodiments wherein the solvent is not an ionic liquid, it is preferred that the non-aqueous electrolyte solution comprises an inorganic or organic salts as electrolyte.

To increase the conversion rate of the furanic compound to the intermediate or maleic acid, it may be preferable that the electrochemical oxidation is carried at a temperature in the range of 10 to 100° C., more preferably in the range of 15 to 70° C. In particular for electrochemical oxidation, it is not common to carry out the oxidation at elevated temperatures (i.e. above room temperature). However, for the present process, it was found that elevated temperatures and in particular temperatures of about 35° to 60° C. do result in an increased conversion rate and yield as well better solubility (i.e. concentration can be increased somewhat).

Although a high concentration of the starting material in the reaction solvent is typically advantageous to achieve a high conversion rate in chemical redox reactions, this is may be less the case for electrochemical oxidation reactions since the rate limiting step is typically mostly determined by the electron density at the electrode and less by the concentration of the reactants in the solution. In other words, the accessible electrode surface area and the electrical current mostly influence the conversion rate. Although a high concentration of the starting material in the reaction solvent is typically advantageous to achieve a high conversion rate in chemical redox reactions, this is may be less the case for electrochemical oxidation reactions. Generally, in such processes, increasing concentration increases the electrical current until the value of the kinetic electrical current, which is determined by the nature of electrode, the surface area of the electrode, the molecule(s) to react, adsorption properties on the electrode and the like. Then the reaction cannot proceed faster. It becomes limited by the exchange of formed product at the electrode with fresh reactant. In other words, the accessible electrode surface area, the electrical current, and the mass transfer typically mostly influence the conversion rate. Therefore, a higher concentration may not necessarily result in an increased reaction rate, and might only result in long reaction times, which may in turn lead to decomposition of reactant(s), intermediates, or product(s). This is particularly undesired for continuous flow reactions wherein full conversion may as such not be reached. Therefore, in the embodiments wherein the process comprises the electrochemical oxidation, it is preferred that the electrochemical oxidation is carried out at a concentration of the furanic compound in the electrolyte solution in the range of 0.01 to 5 mol/L, preferably in the range of 0.1 mol/L to 3.5 mol/L, more preferably in the range of 0.3 mol/L to 2 mol/L. This range gave particular good conversion rates and yields. Since the concentration may decrease in time, with concentration is herein meant the initial concentration of the furanic compound, i.e. the concentration at the start of the reaction.

In a preferably embodiment, the electrochemical oxidation is carried out in a two-compartments electrochemical cell in which the anode electrolyte solution and the cathode electrolyte solution are separated by a membrane (e.g. a semi permeable membrane such as a cation exchange membrane (CEM) or anion exchange membrane (AEM) depending on the specifics of the process). This embodiment is particularly preferable for carrying out the process on large scale as it will prevent or at least limit the reaction product (maleic acid and the oxidation intermediate) being reduced at the cathode, and also because it will prevent or at least limit the furanic compound from crossing over to the cathode, in both which cases efficiency would be reduced. Suitable membranes for this embodiment include membranes available under the tradenames Nafion™, Fumatech™, Neosepta™ and/or Selemion™ and the like. Also, a porous diaphragm/glass frit might be sufficient.

In a preferred embodiment of the present invention, the process further comprises a step of isolating the maleic acid or the derivative thereof to provide the isolated maleic acid or derivative thereof, and a used electrolyte solution. The used electrolyte solution can then be recycled into the process. The used electrolyte solution may contain residual furanic compound, intermediates of the process, maleic acid, and any other impurities and/or polymers that are formed. Accordingly, it may be preferred to purify the used electrolyte solution prior to recycling (e.g. nano-filtration to remove polymeric materials). Alternatively or additionally to the purification, it may be preferred to bleed some of the recycled electrolyte and add fresh material to maintain a constant quality of the electrolyte.

Isolation of the maleic acid or the derivative thereof can be carried out using standard isolation techniques such as distillation and the like. The specifically preferred method of isolation may depend on the used solvent. By isolation of the maleic acid, the pH of the electrolyte solution can also be restored to the original pH, i.e. the pH at the start of the oxidation. As such, no pH adjustment by additives may be required. In case some electrolyte, acid, solvent or water is lost or consumed during the oxidation of the furanic compound or the isolation of the maleic acid, the acid, solvent or water can be replenished during the recycling of the electrolyte solution.

Recycling of the electrolyte solution is particularly preferred when the present process is a continuous process and for instance carried out in a continuous reactor system. The reactor system in which the process is carried out can accordingly comprise a recycle loop for the electrolyte solution. Recycling the electrolyte solution may advantageously result in a minimal chemical waste production and a reduced external input.

Advantageously, the present process may also comprise paired electro-synthesis to enable co-currently an electrochemical reduction, e.g. production of hydrogen from water or conversion of furfural to furfuryl alcohol, at the cathode. It may also be possible to reduce oxygen to water in order to reduce cell voltage and energy consumption.

It may be appreciated that the present electrochemical oxidation is particularly preferred to minimize chemical waste formation. Chemical waste formation can be further suppressed by carrying out the process of the present invention with an electrolyte solution that consists essentially of water, the furanic compound, the acid (as the electrolyte) and possible reaction intermediates and products such as the maleic acid. In other words, although possible, the presence of additives such as salts, stabilization agents, buffers, surfactants and the like is not preferred and the electrolyte solution is preferably free of such additives. An additional advantage of not including a salt in the electrolyte solution is that the maleic acid can directly be obtained as the free acid, and not necessarily as the salt thereof. In industrial applications with maleic acid, the free acid is typically employed and as such, providing the free maleic acid instead of a salt thereof prevents the requirement of an intermediate conversion of the salt into the free acid and the corresponding generation of salt waste.

As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features.

For the purpose of clarity and a concise description features are described herein as part of the same or separate embodiments, however, it will be appreciated that the scope of the invention may include embodiments having combinations of all or some of the features described. The present invention can be illustrated by the following non-limiting examples.

EXAMPLE 1: CONVERSION OF METHYL 2-FUROATE TO MALEIC ACID

The anode compartment of an H-cell was charged with 100 mL of 0.5 M aqueous sulfuric acid containing 10 mM of methyl furoate and 20 mM of vanadium pentoxide. The cathode compartment of the H-cell was charged 100 mL of 0.5 M aqueous sulfuric acid. A 22 cm$^2$ PbO$_2$ electrode was activated by cyclic voltammetry (CV) between 0.8-2.4V against standard hydrogen electrode (SHE). The reference and working electrodes were made ready, then a potential of 1.75V vs. reversible hydrogen electrode (RHE) was applied across the cell. Analysis after 6 hours shows ~42% yield on maleic acid, with residual methyl furoate and reaction intermediate formyl-acrylic acid both present.

EXAMPLE 2: CONVERSION OF 2-FUROIC ACID TO MALEIC ACID—VANADIUM PENTOXIDE MEDIATOR

The anode compartment of an H-cell was charged with 100 mL of 0.5 M aqueous sulfuric acid containing 20 mM of 2-furoic acid and 20 mM of vanadium pentoxide. The cathode compartment of the H-cell was charged 100 ml of 0.5 M aqueous sulfuric acid. A 10 cm$^2$ PbO$_2$ electrode was activated by CV between 0.5-2.1V against SHE. The reference and working electrodes were made ready then a potential of 1.6V vs. saturated calomel electrode SCE was applied across the cell. Analysis after 7 hours shows ~15:4:1 ratio of the reaction intermediate formyl-acrylic acid:maleic acid:2-furoic acid present.

EXAMPLE 3: CONVERSION OF 2-FUROIC ACID TO MALEIC ACID—VANADIUM PENTOXIDE MEDIATOR AND INCREASED CONCENTRATION

The anode compartment of an H-cell was charged with 100 mL of 0.5 M aqueous sulfuric acid containing 50 mM of 2-furoic acid and 20 mM of vanadium pentoxide. The cathode compartment of the H-cell was charged 100 ml of 0.5 M aqueous sulfuric acid. A 10 cm$^2$ PbO$_2$ electrode was activated by CV between 0.8-2.1V against SHE. The reference and working electrodes were made ready, then a galvanostatic current of 0.2 A was applied. Analysis after 15 hours shows ~2:3 ratio of the reaction intermediate formyl-acrylic acid:maleic acid present.

EXAMPLE 4: CONVERSION OF 2-FUROIC ACID TO MALEIC ACID—VANADIUM PENTOXIDE MEDIATOR, INCREASED CONCENTRATION, AND HEATED

The anode compartment of an H-cell was charged with 100 mL of 0.5 M aqueous sulfuric acid containing 50 mM of 2-furoic acid and 20 mM of vanadium pentoxide. The cathode compartment of the H-cell was charged 100 ml of 0.5 M aqueous sulfuric acid. A 10 cm$^2$ PbO$_2$ electrode was activated by CV between 0.8-2.1V against SHE. The reference and working electrodes were made ready, then the contents of the cells were heated to 35° C. A galvanostatic current of 0.2 A was then applied. Analysis after 12 hours shows ~9:11 ratio of the reaction intermediate formyl-acrylic acid:maleic acid being present.

EXAMPLE 5: CONVERSION OF 2-FUROIC ACID TO MALEIC ACID—NO MEDIATOR

The anode compartment of an H-cell was charged with 100 mL of 0.5 M aqueous sulfuric acid containing 20 mM of 2-furoic acid. The cathode compartment of the H-cell was charged 100 ml of 0.5 M aqueous sulfuric acid. A 10 cm$^2$ PbO$_2$ electrode was activated by CV between 0.5-2.1V against SHE. The reference and working electrodes were made ready, then a potential of 1.84 V vs. SCE was applied across the cell. Analysis after 19 hours shows ~25:74:1 ratio of the reaction intermediate formyl-acrylic acid:maleic acid:2-furoic acid being present.

EXAMPLE 6: CONVERSION OF FURFURAL TO MALEIC ACID—VANADIUM PENTOXIDE MEDIATOR

The anode compartment of an H-cell was charged with 100 mL of 0.5 M aqueous sulfuric acid containing 20 mM of furfural and 20 mM of vanadium pentoxide. The cathode compartment of the H-cell was charged 100 ml of 0.5 M aqueous sulfuric acid. A 10 cm$^2$ PbO$_2$ electrode was activated by CV between 0.5-2.1V against SHE. The reference and working electrodes were made ready then a potential of 1.6 V vs. SCE was applied across the cell. Analysis after 19 hours shows ~5:1 ratio of the reaction intermediate formyl-acrylic acid:maleic acid present.

EXAMPLE 7: CONVERSION OF FURFURAL TO MALEIC ACID—VANADIUM PENTOXIDE MEDIATOR

The anode compartment of an H-cell was charged with 100 mL of 0.5 M aqueous sulfuric acid containing 40 mM of furfural and 20 mM of vanadium pentoxide. The cathode compartment of the H-cell was charged 100 ml of 0.5 M aqueous sulfuric acid. A 10 cm$^2$ PbO$_2$ electrode was activated by CV between 0.5-2.1V against SHE. The reference and working electrodes were made ready then a potential of 1.9 V vs. SCE was applied across the cell. Analysis after 12 hours shows ~80% yield of maleic acid present.

EXAMPLE 8: CONVERSION OF FURFURAL TO 5-HYDROXY-2(5H)-FURANONE

The anode compartment of an H-cell was charged with 100 mL of 0.5 M aqueous sulfuric acid containing 50 mM of furfural. Conversion at 20° C. The cathode compartment of the H-cell was charged 100 ml of 0.5 M aqueous sulfuric acid. A 10 cm$^2$ PbO$_2$ electrode was activated by CV between 0.5-2.1V against SHE. The reference and working electrodes were made ready then a potential of 1.85 V vs. SCE was applied across the cell. Analysis after 7 hours shows ~2:1 ratio of the reaction intermediate formyl-acrylic acid:maleic acid present, and ~9:1 after 20 hours. The maximum total yield of the product (maleic acid and 5-hydroxy-2(5H)-furanone is ~80%).

EXAMPLE 9: CONVERSION OF FURFURAL TO 5-HYDROXY-2(5H)-FURANONE

The anode compartment of an H-cell was charged with 100 mL of 0.5 M aqueous sulfuric acid containing 50 mM of furfural. Conversion at 35° C. The cathode compartment of the H-cell was charged 100 ml of 0.5 M aqueous sulfuric acid. A 10 cm² PbO$_2$ electrode was activated by CV between 0.5-2.1V against SHE. The reference and working electrodes were made ready then a potential of 1.85 V vs. SCE was applied across the cell. Analysis after 7 hours shows ~1:2 ratio of the reaction intermediate formyl-acrylic acid:maleic acid present, and ~1:10 after 20 hours. The maximum total yield of the product (maleic acid and 5-hydroxy-2(5H)-furanone is ~70%).

EXAMPLE 10: CONVERSION OF FURFURAL TO 5-HYDROXY-2(5H)-FURANONE

The anode compartment of an H-cell was charged with 100 mL of 0.5 M aqueous sulfuric acid containing 50 mM of furfural. Conversion at 50° C. The cathode compartment of the H-cell was charged 100 ml of 0.5 M aqueous sulfuric acid. A 10 cm² PbO$_2$ electrode was activated by CV between 0.5-2.1V against SHE. The reference and working electrodes were made ready then a potential of 1.85 V vs. SCE was applied across the cell. Analysis after 7 hours shows ~1:34 ratio of the reaction intermediate formyl-acrylic acid:maleic acid present.

EXAMPLE 11: EXTRACTION OF CIS-β-FORMYLACRYLIC ACID/5-HYDROXY-2(5H)-FURANONE AND MALEIC ACID FROM ELECTROLYTE

An equal volume of the electrolyte from Example 9 and an organic solvent (Ethyl acetate, Dichloromethane, Toluene, 2-Methyltetrahydrofuran, Diethyl Ether) were mixed together intensely and then left to phase separate. Both the aqueous and organics phases were then analysed by HPLC to determine the relative levels of cis-β-formylacrylic acid/5-hydroxy-2(5H)-furanone and maleic acid in each of the phases:

|  | Aqueous Phase | | Organic Phase | |
| --- | --- | --- | --- | --- |
|  | Furanone | Maleic Acid | Furanone | Maleic Acid |
| Ethyl Acetate | 8.3% | 54.8% | 91.7 | 45.2% |
| Dichloromethane | 99.1% | 100% | 0.9% | 0% |
| Toluene | 99.1% | 100% | 0.9% | 0% |
| 2-MethylTHF | 41.3% | 26.4% | 58.7% | 73.6% |
| Diethyl Ether | 65.9% | 63.2% | 34.1% | 36.6% |

The conditions using ethyl acetate were scaled up, with the organic phase being separated from the aqueous, dried over sodium sulfate, then concentrated in vacuo to yield a white solid product (400 mg). This was analyzed by NMR and confirmed to be a ~2.7:1 ratio of cis-β-formylacrylic acid/5-hydroxy-2(5H)-furanone:maleic acid.

EXAMPLE 12: OXIDATION OF CIS-β-FORMYLACRYLIC ACID/5-HYDROXY-2(5H)-FURANONE TO MALEIC ACID/ANHYDRIDE

To two separate reactors were charged the cis-β-formylacrylic acid/5-hydroxy-2(5H)-furanone:maleic acid mixture isolated in Example 11 (50 mg), 5% palladium on carbon (25 mg), and solvent (350 µL—either 0.5 M aqueous sulfuric acid, pH 7 aqueous buffer solution of monopotassium phosphate and dipotassium phosphate). The reactors were then heated to 70° C. with stirring and oxygen was bubbled through the mixture. After 2 hours, the reactions were cooled to room temperature and analyzed by HPLC. In both cases, conversion of cis-β-formylacrylic acid/5-hydroxy-2(5H)-furanone to maleic acid.

EXAMPLE 14: SOLVENTS FOR THE OXIDATION OF HFO TO MALEIC ACID

An autoclave (10 ml) was charged with HFO, solvent (1 ml) and 10% Pd/C according to the Table 1 below.

The reactor was sealed then flushed with nitrogen. The reactor was then charged to 10 bar of pressure with pure oxygen. The reactor was then heated to 85° C. and stirred for 15 hours. After cooling to ambient temperature, the pressure was released and the reactor flushed with nitrogen. The product solutions were then filtered to remove catalyst, then analyzed by high-performance liquid chromatography (HPLC), with the yield of maleic acid compiled in Table 1.

TABLE 1

| Solvent | HFO (mg) | Pd/C (mg) | TOF/sec for MA* |
| --- | --- | --- | --- |
| Water | 10.0 | 5.7 | 0 |
| 0.5M Sulfuric Acid | 8.3 | 4.1 | 0 |
| Ethyl Acetate | 7.0 | 9.1 | 155 |
| Methylisobutylketone | 5.5 | 4.4 | 265 |
| Methyl-t-butyl ether | 5.8 | 5.1 | 321 |
| 2-MeTHF | 7.1 | 4.4 | 790 |
| Dichloromethane | 6.6 | 8.5 | 0 |
| Acetic Acid | 6.5 | 7.3 | 10 |
| n-Heptane | 6.0 | 3.7 | 276 |
| Toluene | 4.6 | 4.4 | 738 |
| Acetonitrile | 5.3 | 12.0 | 43 |
| Acetone | 4.6 | 12.0 | 108 |
| Dimethyl Carbonate | 5.4 | 4.1 | 115 |
| Nitromethane | 5.3 | 4.7 | 86 |

*TOF/sec for MA means turnover frequency of the catalyst for MA under those conditions

EXAMPLE 15: CATALYSTS FOR THE OXIDATION OF HFO TO MALEIC ACID IN TOLUENE

An autoclave (10 ml) was charged with HFO (10.6 mg), toluene (1 ml) and catalyst according to the Table 2. The reactor was sealed then flushed with nitrogen. The reactor was then charged to 10 bar of pressure with pure oxygen. The reactor was then heated to 111° C. and stirred for 14 hours. After cooling to ambient temperature, the pressure was released and the reactor flushed with nitrogen. The product solutions were then filtered to remove catalyst, then analyzed by HPLC, with the results compiled in Table 2.

TABLE 2

| Solvent | Catalyst (mg) | TOF/sec for MA |
| --- | --- | --- |
| No Catalyst | — | 0 |
| Au/SiO2 | 94 | 3279 |
| Pd/C | 6.0 | 309 |
| Pt/C | 13 | 82 |
| Ru/C | 11 | 1464 |

* TOF/sec for MA means turnover frequency of the catalyst for MA under those conditions

The invention claimed is:
1. A process for the preparation of maleic acid, or a derivative thereof selected from the group consisting esters of maleic acid, amides of maleic acid, maleimides, anhy- drides of maleic acid, and maleic anhydride, said process comprising a first step comprising an electrochemical oxidation in an electrolyte solution of a furanic compound into one or more intermediates; wherein said furanic compound is a compound according to formula I of which $R^1$ is H, $CH_2OH$, $CO_2H$ or CHO and $R^2$ is or an ester, ether, amide, acid halide, anhydride, carboximidate, nitrile, or salts of said compound according to formula I;

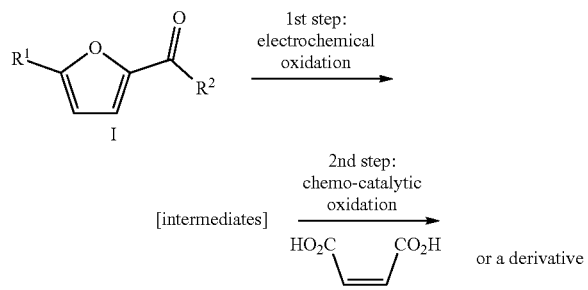

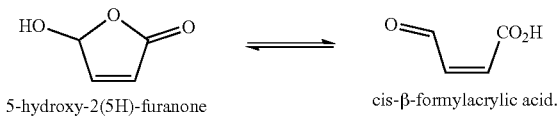

or a derivative a second step which follows the first step and comprises a chemo-catalytic oxidation of said intermediates to provide maleic acid or the derivative thereof, which chemo-catalytic oxidation is a non-electrochemical oxidation.

2. The process according to claim 1, wherein said one or more intermediates comprise 5-hydroxy-2(5H)-furanone and/or cis-β-formylacrylic acid 3. The process according to claim 1, wherein the electrolyte solution is essentially free of a mediator.

4. The process according to claim 1, wherein the chemo-catalytic oxidation is carried out by using oxygen as an oxidation agent in the presence of a catalyst.

5. The process according to claim 1, further comprising an extraction of said intermediates with an organic solvent and carrying out said second step in said organic solvent.

6. The process according to claim 1, wherein said second step directly provides maleic anhydride

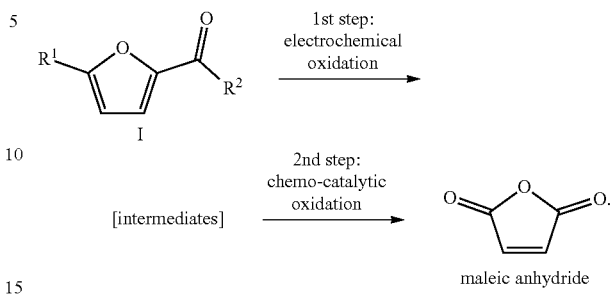

maleic anhydride

7. The process according to claim 1, wherein said first step comprises photoelectrochemical oxidation.

8. The process according to claim 1, wherein said electrolyte solution is an aqueous electrolyte solution.

9. The process according to claim 1, wherein the electrolyte solution comprises an acid.

10. The process according to claim 1, wherein the electrochemical oxidation is carried out at a pH of less than 4.

11. The process according to claim 1, wherein the electrochemical oxidation is carried out at an initial concentration of the furanic compound in the electrolyte solution in the range of 0.01 to 5 mol/L.

12. The process according to claim 1, wherein the chemo-catalytic oxidation is carried out at a temperature in the range of 20 to 150° C.

13. The process according to claim 1, wherein said electrochemical oxidation is carried out with one or more working electrodes comprising lead oxide and/or boron doped diamond (BDD).

14. The process according to claim 1, further comprising a step of isolating the maleic acid or the derivative thereof to provide the isolated maleic acid or derivative thereof and a used electrolyte solution.

15. The process according to claim 1, which process is a continuous process which is carried out in a continuous reactor system.

16. The process according to claim 1, wherein at the start of the process, the electrolyte solution essentially consists of only water, the furanic compound, an acid, and optionally an inorganic salt.

* * * * *